United States Patent [19]
Tice et al.

[11] Patent Number: 6,117,821
[45] Date of Patent: Sep. 12, 2000

[54] N-(HETEROCYCLYLCARBONYL) SULFONAMIDE HERBICIDES

[75] Inventors: Colin Michael Tice, Elkins Park, Pa.; Bin Li, Shenyang, China

[73] Assignee: Rohm and Haas Company, Phila., Pa.

[21] Appl. No.: 09/309,432

[22] Filed: May 11, 1999

Related U.S. Application Data

[60] Provisional application No. 60/086,263, May 21, 1998.
[51] Int. Cl.[7] .................. A01N 43/40; C07D 405/06; C07D 213/56; C07D 213/81; C07D 213/82
[52] U.S. Cl. .................. 504/244; 546/316; 546/323; 546/281.7
[58] Field of Search ................... 546/281.7, 316, 546/323; 504/244

[56] References Cited

U.S. PATENT DOCUMENTS 4,157,257   6/1979   Takematsu et al. ................. 504/333

OTHER PUBLICATIONS

Phytotoxic Activity of N–Phenylsulfonylbenzamides, K. Yoneyama, et al., *Agric. Biol. Chem.*, 47 (3), 593–596, 1983.

*Primary Examiner*—Alan L. Rotman
*Attorney, Agent, or Firm*—Clark R. Carpenter

[57] ABSTRACT

This invention relates to herbicidal N-(heterocyclylcarbonyl)sulfonamide compounds, compositions comprising N-(heterocyclylcarbonyl)sulfonamide herbicides and an agronomically acceptable carrier, and the use thereof as broad spectrum herbicides which are effective against both monocot and dicot weed species in both preemergence and postemergence applications. This invention also teaches methods of preparing these compounds as well as methods of using the compounds as herbicides.

9 Claims, No Drawings

N-(HETEROCYCLYLCARBONYL) SULFONAMIDE HERBICIDES

This application claims benefit of Provisional Application Serial No. 60/086,263 filed May 21, 1998.

The need continues for novel and improved herbicidal compositions. This is particularly so since the targets of herbicides can become resistant to known herbicides over time and after use of such compositions. Additionally, economic and environmental considerations can favor herbicides having different modes of performance than those currently used. This invention relates to herbicidal N-(heterocyclylcarbonyl)sulfonamide compounds, compositions comprising N-(heterocyclylcarbonyl)sulfonamide herbicides and an agronomically acceptable carrier, and the use thereof as broad spectrum herbicides which are effective against both monocot and dicot weed species in both preemergence and postemergence applications. This invention also teaches methods of preparing these compounds as well as methods of using the compounds as herbicides.

Yoneyama et al. in *Agric. Biol. Chem.*, 47, 593–596 (1983) and Takematsu et al. in U.S. Pat. No. 4,157,257, Jun. 5, 1979 both describe substituted N-(phenylsulfonyl) benzamide compounds which possess herbicidal activity. However, the N-(heterocyclylcarbonyl)sulfonamide herbicides of the present invention are neither disclosed nor suggested.

One embodiment of this invention relates to a compound of the formula

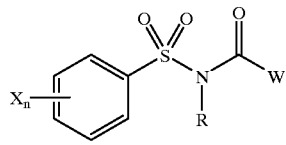

wherein

W is a heterocyclyl moiety selected from pyridyl, pyrazinyl, pyrimidinyl, pyridazinyl, furyl and thienyl, all substituted with a halo($C_1$–$C_6$)alkyl vicinal to the carbonyl group, and all optionally further substituted with from 1 to 3 substituents selected from Z, R is ($C_3$–$C_6$)alkynyl or epoxy($C_3$–$C_6$)alkyl, n is 0, 1, 2, or 3, and X and Z are each independently halo, ($C_1$–$C_6$)alkyl, halo($C_1$–$C_6$)alkyl, ($C_1$–$C_6$)alkoxy, halo($C_1$–$C_6$)alkoxy, nitro, cyano or ($C_1$–$C_6$)alkoxycarbonyl.

In a preferred mode of this embodiment, W is pyridyl substituted with trifluoromethyl vicinal to the carbonyl group, R is propargyl or 2,3-epoxypropyl, n is 1, and X and Z are each independently halo or methyl.

In a more preferred mode of this embodiment, W is 4-(trifluoromethyl)-3-pyridyl, R is propargyl, and X is 3-chloro or 3-methyl.

As used in the present invention, ($C_1$–$C_6$)alkyl means a straight or branched alkyl chain and includes, for example, methyl, ethyl, n-propyl, isopropyl, n-butyl, sec-butyl, tert-butyl, n-pentyl and n-hexyl. ($C_1$–$C_6$)alkoxy means a linear or branched alkoxy group and includes, for example, methoxy, ethoxy, isopropoxy and n-propoxy. Halo is fluoro, chloro, bromo or iodo. Halo($C_1$–$C_6$)alkyl means a linear or branched alkyl group substituted with one or more halo and includes, for example, trifluoromethyl, perfluoroethyl and 2,2,2-trifluoroethyl. Halo($C_1$–$C_6$)alkoxy means a linear or branched alkoxy group substituted with one or more halo and includes, for example, trifluoromethoxy, perfluoroethoxy and chloromethoxy. ($C_1$–$C_6$)alkoxycarbonyl means a linear or branched alkoxy group attached to a carbonyl group and includes, for example, methoxycarbonyl and ethoxycarbonyl. ($C_3$–$C_6$)alkynyl means a linear or branched alkynyl group and includes, for example, propargyl and 2-butynyl. Epoxy($C_3$–$C_6$)alkyl means a straight or branched alkyl chain and includes, for example, n-propyl, isopropyl, n-butyl, isobutyl, sec-butyl, n-pentyl, n-hexyl on which an oxygen atom is linked to adjacent carbon atoms and includes, for example, 2,3-epoxypropyl and 2,3-epoxybutyl.

Another embodiment of this invention relates to a N-(heterocyclylcarbonyl)sulfonamide herbicidal composition comprising a herbicidally effective amount of a compound of formula (I) and an agronomically acceptable carrier.

Yet another embodiment of this invention relates to a method of controlling a weed comprising applying a herbicidally effective amount of a composition comprising a N-(heterocyclylcarbonyl)sulfonamide compound of formula (I) and an agronomically acceptable carrier to the weed, to the locus of the weed or to the growth medium of said weed.

According to the present invention, the compound of formula (I) is produced by reacting a benzenesulfonamide derivative of formula (II)

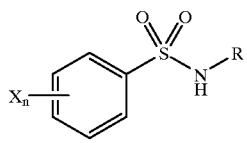

with a heterocyclic carbonyl chloride of formula (III)

wherein W, $X_n$ and R have the same meanings as in formula (I). The compounds of formula (II) and (III) are either available commercially or are able to be synthesized by methods known to one of ordinary skill in the art.

The reaction of the benzenesulfonamide derivative of formula (II) with the heterocyclic carbonyl chloride of formula (III) can be carried out in the presence or absence of a solvent. Generally, a solvent which is inert to the reaction conditions is preferred. Examples of usable solvents are water, ethers, aromatic hydrocarbons, N,N-dimethylformamide, dimethyl sulfoxide, pyridine and mixtures thereof.

The reaction temperature is not critical, but is generally from about 0° C. to about the reflux temperature of the reaction mixture. Pressure is also not critical and atmospheric pressure is most usually employed. Reaction times are typically from about 30 minutes to about 6 hours.

The ratio between the benzenesulfonamide derivative of formula (II) to the heterocyclic carbonyl chloride of formula (III) is not critical, but generally a slight excess of the benzenesulfonamide derivative of formula (II) is used, preferably a 5–20% molar excess.

The reaction is most usually carried out in the presence of a base which acts as an acid sink. Convenient bases for this purpose include alkali metal hydroxides, for example sodium and potassium hydroxide, and organic bases, for example pyridine and triethylamine. The amount of the alkali metal hydroxide or the organic base is usually in excess amount relative to the heterocyclic carbonyl chloride of formula (III). From about a 10% to about a 200% molar excess of the base is conveniently utilized.

The following examples, tables and experimental procedures are provided for guidance to the practitioner and are not meant to limit the scope of the invention which is defined by the claims.

TABLE 1

Prepared Compounds

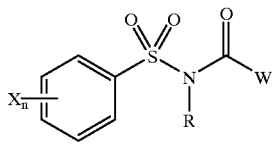

(I)

| Example | R | $X_n$ | W |
|---|---|---|---|
| 1 | $CH_2C\equiv CH$ | 3-Cl | 4-$CF_3$-3-pyridyl |
| 2 | $CH_2C\equiv CH$ | 3-Cl | 2-$CF_3$-5-$CH_3$-3-furyl |
| 3 | $CH_2C\equiv CH$ | 3-$CH_3$ | 4-$CF_3$-3-pyridyl |
| 4 | $CH_2C\equiv CH$ | 3-Cl | 2-Cl-4-$CF_3$-5-pyrimidinyl |

EXAMPLE 1

Preparation of 3-chloro-N-propargyl-N-(4-(trifluoromethyl)pyridine-3-carbonyl) benzenesulfonamide To a stirred, ice cold solution of 3-chloro-N-propargylbenzenesulfonamide (3.0 g, 13 mmol) in 40 mL of tetrahydrofuran (THF), sodium hydride (0.6 g, 60% by wt. in oil, 14 mmol) was added portionwise over 5 min. The mixture was stirred for 20 min and a solution of 4-(trifluoromethyl)pyridine-3-carbonyl chloride (2.7 g, 13 mmol) in 10 mL of THF was added dropwise over 5 min. The mixture was stirred at room temperature for 10 h. The mixture was poured into ethyl acetate (100 mL) and water (100 mL). The layers were separated and the aqueous layer was extracted with ethyl acetate (2×50 mL). The combined organic layers were washed with saturated aqueous NaHCO$_3$, water and brine, and dried over Na$_2$SO$_4$. Removal of the solvent afforded 4.0 g of an oil. Chromatography on silica gel (100 g) eluting with 25% ethyl acetate in hexane afforded 2.5 g of 3-chloro-N-propargyl-N-(4-(trifluoromethyl)pyridine-3-carbonyl)benzenesulfonamide, mp=82–85° C.

EXAMPLE 2

Preparation of 3-chloro-N-propargyl-N-(5-methyl-2-(trifluoromethyl)furan-3-carbonyl) benzenesulfonamide Using essentially the procedure described in Example 1 except for the substitution of 5-methyl-2-(trifluoromethyl)furan-3-carbonyl chloride for the 4-(trifluoromethyl)pyridine-3-carbonyl chloride, 3-chloro-N-propargyl-N-(5-methyl-2-(trifluoromethyl)furan-3-carbonyl)benzenesulfonamide was prepared, mp=70–72° C.

EXAMPLE 3

Preparation of 3-methyl-N-propargyl-N-(4-(trifluoromethyl)pyridine-3-carbonyl) benzenesulfonamide To a stirred, ice cold solution of 3-methyl-N-propargylbenzenesulfonamide (2.1 g, 10 mmol) in 40 mL of THF, sodium hydride (0.4 g, 60% by wt. in oil, 10 mmol) was added portionwise over 5 min. The mixture was stirred for 20 min and a solution of 4-(trifluoromethyl)pyridine-3-carbonyl chloride (1.5 g, 7 mmol) in 10 mL of THF was added dropwise over 5 min. The mixture was stirred at room temperature for 10 h. The mixture was poured into ethyl acetate (50 mL) and water (50 mL). The layers were separated and the aqueous layer was extracted with ethyl acetate (2×25 mL). The combined organic layers were washed with saturated aqueous NaHCO$_3$, water and brine, and dried over Na$_2$SO$_4$. Removal of the solvent afforded 2.0 g of a solid. Chromatography on silica gel (70 g) eluting with 25% ethyl acetate in hexane afforded 1.2 g of 3-methyl-N-propargyl-N-(4-(trifluoromethyl)pyridine-3-carbonyl) benzenesulfonamide, mp=111–114° C.

EXAMPLE 4

Preparation of 3-chloro-N-propargyl-N-(2-chloro-4-(trifluoromethyl)pyrimidine-5-carbonyl) benzenesulfonamide Using essentially the procedure described in Example 1 except for the substitution of 2-chloro-4-(trifluoromethyl)pyrimidine-5-carbonyl chloride for the 4-(trifluoromethyl)pyridine-3-carbonyl chloride, 3-chloro-N-propargyl-N-(2-chloro-4-(trifluoromethyl)pyrimidine-5-carbonyl) benzenesulfonamide was prepared, mp=106–107° C.

Biological Test Methods

The preemergence tests were run using plastic trays measuring (W×L×H) 20×30×8 cm. The soil was locally obtained, Pennsylvania top soil (silty loam with 1.0 to 1.5% organic matter). The sub-soil (soil below the seed) in the tray was amended with Redi-Earth™ in a one to one ratio. Cover soil (soil above the seed) was amended with sand in a two soil and one sand mix. Seeds were sown 1.27 cm deep.

Postemergence tests weeds in the primary screens were on plants grown in 7.62 or 10.16 cm diameter pots. The soil used was amended with Redi-Earth in a one to one ratio. Generally, postemergence plants were 7 to 21 days old (from planting) when sprayed. Grasses were in the 2–4 leaf stage and broadleaf weeds were in the 1–2 true leaf stage.

The normal spray volumes were either 25 or 50 gallons per acre (234 or 468 L/Ha). Rates of application (grams per hectare) varied depending on the concentration of chemical within each individual spray solution. Technical samples were usually dissolved in acetone. All applications were made using a trolley belt sprayer. The test plants were placed on the belt inside the spray hood. Then the spray nozzle, which is attached to the trolley, moved mechanically over the top of the plants. The spray nozzle delivered a flat fan spray pattern and was a typical nozzle used in herbicide field applications. The belt carried the plants out of the spray hood and into a drying chamber.

After spray application, the test plants were placed in a vented cabinet until dry, then placed in the greenhouse. The preemergence tests were watered overhead and postemergence tests were watered by subirrigation for a period of 48 hours so that the water did not contact the foliage.

Test observations were made 2 to 3 weeks after treatment using a 0% (no effect) to 100% (complete control) rating system. The percent injury values were a composite value which entailed chlorosis, necrosis, inhibition of growth, or tip burning. All ratings were made compared to an untreated check and are shown in Tables 2a and 2b:

TABLE 2a

Preemergence Activity

| Example | Dose (g/Ha) | BID | NS | SMT | VEL | BYG | CRB | FOX | RYE |
|---|---|---|---|---|---|---|---|---|---|
| 1 | 2400 | 0 | 0 | 0 | 15 | 100 | 100 | 100 | 0 |
| 2 | 2400 | 20 | 20 | 50 | 10 | 0 | 0 | 0 | 0 |
| 3 | 1200 | 0 | 0 | 0 | 0 | 100 | 100 | 100 | 0 |
| 4 | 2400 | 0 | 0 | 0 | 0 | 0 | 0 | 0 | 0 |

TABLE 2b

Postemergence Activity

| Example | Dose (g/ha) | BID | NS | SMT | VEL | BYG | CRB | FOX | RYE |
|---|---|---|---|---|---|---|---|---|---|
| 1 | 2400 | 0 | 20 | 15 | 25 | 95 | 60 | 90 | 0 |
| 2 | 2400 | 0 | 0 | 0 | 0 | 0 | 0 | 0 | 0 |
| 3 | 1200 | 0 | 40 | 0 | 30 | 85 | 20 | 35 | 0 |
| 4 | 2400 | 25 | 15 | 0 | 15 | 0 | 0 | 35 | 0 |

TABLE 3a

Key to Weed Species - Grasses

| Abbreviation | Common Name | Scientific Name |
|---|---|---|
| BYG | Barnyardgrass | *Echinochloa crus-galli* |
| CRB | Crabgrass (large) | *Digitaria sanguinalis* |
| FOX | Foxtail, green | *Setaria viridis* |
| RYE | Perennial Ryegrass | *Lolium perenne* |

TABLE 3b

Key to Weed Species - Broad Leaves

| Abbreviation | Common Name | Scientific Name |
|---|---|---|
| BID | Hairy Beggarticks | *Bidens pilosa* |
| NS | Nightshade, black | *Solanum nigrum* |
| SMT | Smartweed, pale | *Polygonum lapathifolium* |
| VEL | Velvetleaf | *Abutilon theophrasti* |

The N-(heterocyclylcarbonyl)sulfonamide compounds and compositions of this invention are useful as both preemergence and postemergence herbicides. Preemergence herbicides are applied before the plants have emerged from the soil. Postemergence herbicides are applied after the plants have emerged and during their growth period. The embodied materials generally show selectivity to several agronomically important crops such as corn, cotton, rice, soybean and wheat.

The N-(heterocyclylcarbonyl)sulfonamide compositions of the present invention can be applied to various loci such the soil or the foliage. For such purposes these compositions can be used as solutions or as formulations. The compounds comprising the compositions are usually taken up in a carrier or are formulated so as to render them suitable for subsequent dissemination as herbicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual." Allured Publishing Company, Ridgewood, N.J., U.S.A.

The N-(heterocyclylcarbonyl)sulfonamide compositions can be applied as herbicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and weeds to be controlled, but the preferred effective amount is usually from about 150 to about 4800 g/Ha of the active ingredient, more preferably from about 600 to about 3600 g/Ha.

The N-(heterocyclylcarbonyl)sulfonamide compositions of the invention can also be mixed with fertilizers or fertilizing materials before their application. In one type of solid fertilizing composition in which the N-(heterocyclylcarbonyl)sulfonamide compounds can be used, particles of a fertilizer or fertilizing ingredients, such as ammonium sulfate, ammonium nitrate, or ammonium phosphate, can be coated with one or more of the compounds. The solid compounds and solid fertilizing material can also be admixed in mixing or blending equipment, or they can be incorporated with fertilizers in granular formulations. Any relative proportion of fertilizer can be used which is suitable for the crops and weeds to be treated. The N-(heterocyclylcarbonyl)sulfonamide compound will commonly be from about 5% to about 25% of the fertilizing composition. These compositions provide fertilizing materials which promote the rapid growth of desired plants, and at the same time control the growth of undesired plants.

For some applications, one or more other herbicides may be added to the compositions of the present invention, thereby providing additional advantages and effectiveness. When mixtures of herbicides are employed, the relative proportions which are used will depend upon the relative efficacy of compounds in the mixture with respect to the plants to be treated. Examples of other herbicides which can be combined with those of the present invention include:

CARBOXYLIC ACIDS AND DERIVATIVES 2,3,6-trichlorobenzoic acid and its salts;
2,3,5,6-tetrachlorobenzoic acid and its salts;
2-methoxy-3,5,6-trichlorobenzoic acid and its salts;
2-methoxy-3,6-dichlorobenzoic acid and its salts;
2-methyl-3,6-dichlorobenzoic acid and its salts;
2,3-dichloro-6-methylbenzoic acid and its salts;
2,4-dichlorophenoxyacetic acid and its salts and esters;
2,4,5-trichlorophenoxyacetic acid and its salts and esters;
2-methyl-4-chlorophenoxyacetic acid and its salts and esters;
2-(2,4,5-trichlorophenoxy)propionic acid and its salts and esters;
4-(2,4-dichlorophenoxy)butyric acid and its salts and esters;
4-(2-methyl-4-chlorophenoxy)butyric acid and its salts and esters;
2,3,6-trichlorophenylacetic acid and its salts;
3,6-endoxohexahydrophthalic acid and its salts;
dimethyl 2,3,5,6-tetrachloroterephthalate; trichloroacetic acid and its salts;
2,2-dichloropropionic acid and its salts;
2,3-dichloroisobutyric acid and its salts;
isopropylammonium 2-(4-isopropyl-4-methyl-5-oxo-2-imidazolin-2-yl)nicotinate;

2-[4,5-dihydro-4-methyl-4-(1-methylethyl)-5-oxo-1H-imidazol-2-yl]-3-quinolinecarboxylic acid;
6-(4-isopropyl-4-methyl-5-oxo-2-imidazolin-2-yl)-m-toluic acid, methyl ester;
6-(4-isopropyl-4-methyl-5-oxo-2-imidazolin-2-yl)-p-toluic acid, methyl ester;
N-(phosphomethyl)glycine isopropylammonium salt;
[3,5,6-trichloro-(2-pyridinyl)oxy]acetic acid;
3,7-dichloro-8-quinolinecarboxylic acid;
ammonium DL-homoalanin-4-yl(methyl)phosphinate;

CARBAMIC ACID DERIVATIVES ethyl N,N-di(n-propyl)thiolcarbamate;
n-propyl N,N-di(n-propyl)thiolcarbamate;
ethyl N-ethyl-N-(n-butyl)thiolcarbamate;
n-propyl N-ethyl-N-(n-butyl)thiolcarbamate;
2-chloroallyl N,N-diethyldithiocarbamate;
isopropyl N-phenylcarbamate;
isopropyl N-(m-chlorophenyl)carbamate;
4-chloro-2-butynyl-N-(m-chlorophenyl)carbamate;
methyl N-(3,4-dichlorophenyl)carbamate;
dinitro-o-(sec-butyl)phenol and its salts;
pentachlorophenol and its salts
S-(4-chlorobenzyl)-N,N-diethylthiolcarbamate;

SUBSTITUTED UREAS 2-chloro-N-[(4-methoxy-6-methyl-1,3,5-triazin-2-yl)aminocarbonyl]benzenesulfonamide;
3-(3,4-dichlorophenyl)-1,1-dimethylurea;
3-phenyl-1,1-dimethylurea;
3-(3,4-dichlorophenyl)-3-methoxy-1,1-dimethylurea;
3-(4-chlorophenyl)-3-methoxy-1,1-dimethylurea;
3-(3,4-dichlorophenyl)-1-n-butyl-1-methylurea;
3-(3,4-dichlorophenyl)-1-methoxy-1-methylurea;
3-(4-chlorophenyl)-1-methoxy-1-methylurea;
3-(3,4-dichlorophenyl)-1,1,3-trimethylurea;
3-(3,4-dichlorophenyl)diethylurea;
N-(4-isopropylphenyl)-N,N'-dimethylurea;
dichloral urea;
methyl 2-[[[[(4,6-dimethyl-2-pyrimidinyl)amino]carbonyl]amino]sulfonyl]benzoate;
N-((6-methoxy-4-methyl-1,3,5-triazin-2-yl)aminocarbonyl)-2-(2-chloroethoxy)benzenesulfonamide;
2-[[[(4-chloro-6-methoxypyrimidine-2-yl)aminocarbonyl]amino]sulfonyl]benzoic acid, ethyl ester;
methyl 2-[[[[(4-methoxy-6-methyl-1,3,5-triazin-2-yl)amino]carbonyl]amino]sulfonyl]benzoate;
methyl 3-[[(4-methoxy-6-methyl-1,3,5-triazin-2-yl)aminocarbonyl]aminosulfonyl]-2-thiophenecarboxylate;
methyl 2-[[[[[(4,6-dimethoxypyrimidin-2-yl)amino]carbonyl]amino]sulfonyl]methyl]benzoate;
methyl 2-[[[[(4-methoxy-6-methyl-1,3,5-triazin-2-yl)methylamino]carbonyl]amino]sulfonyl]benzoate;

SUBSTITUTED TRIAZINES 2-chloro-4,6-bis(ethylamino)-s-triazine;
2-chloro-4-ethylamino-6-isopropylamino-s-triazine;
2-chloro-4,6-bis(3-methoxy-n-propylamino)-s-triazine;
2-methoxy-4,6-bis(isopropylamino)-s-triazine;
2-chloro-4-ethylamino-6-(3-methoxy-n-propylamino)-s-triazine;
2-methylmercapto-4,6-bis(isopropylamino)-s-triazine;
2-methylmercapto-4,6-bis(ethylamino)-2-triazine;
2-methylmercapto-4-ethylamino-6-isopropylamino-s-triazine;
2-chloro-4,6-bis(isopropylamino)-s-triazine;
2-methoxy-4-ethylamino-6-isopropylamino-s-triazine;
2-methylmercapto-4-(2-methoxyethylamino)-6-isopropylamino-s-triazine;
4-amino-6-(t-butyl)-3-(methylthio)-1,2,4-triazine-5(4H)-one;

DIPHENYL ETHER DERIVATIVES 2,4-dichloro-4'-nitrodiphenyl ether;
2,4,6-trichloro-4'-nitrodiphenyl ether;
2,4-dichloro-6-fluoro-4'-nitrodiphenyl ether;
3-methyl-4'-nitrodiphenyl ether;
3,5-dimethyl-5'-nitrodiphenyl ether;
2,4'-dinitro-4-(trifluoromethyl)diphenyl ether;
2,4-dichloro-3'-methoxy-4'-nitrodiphenyl ether;
sodium 5-(2-chloro-4-(trifluoromethyl)phenoxy)-2-nitrobenzoate;
2-chloro-1-(3-ethoxy-4-nitrophenoxy)-4-(trifluoromethyl)benzene;
1-(carboethoxy)ethyl 5-[2-chloro-4-(trifluoromethyl)phenoxy]-2-nitrobenzoate;
5-[2-chloro-4-(trifluoromethyl)phenoxyl]-N-(methylsulphony)-2-nitrobenzamide;

ANILIDES 2-chloro-N-(2-ethyl-6-methylphenyl)-N-(2-methoxy-1-methylethyl)acetamide;
2-chloro-2',6'-diethyl-N-(2-propyloxyethyl)acetanilide;
N-(3,4-dichlorophenyl)propionamide;
N-(3,4-dichlorophenyl)methacrylamide;
N-(3-chloro-4-methylphenyl)-2-methylpentanamide;
N-(3,4-dichlorophenyl)trimethylacetamide;
N-(3,4-dichlorophenyl)-α,α-dimethylvaleramide;
N-isopropyl-N-phenylchloroacetamide;
N-n-butoxymethyl-N-(2,6-diethylphenyl)chloroacetamide;
N-methoxymethyl-N-(2,6-diethylphenyl)chloroacetamide;

OXYPHENOXY HERBICIDES 2-(4-(2,4-dichlorophenoxy)phenoxy)methyl propionate;
methyl 2-(4-(3-chloro-5-(trifluoromethyl)-2-pyridinyloxy)phenoxy)propanoate;
butyl (R)-2-[4-[5-(trifluoromethyl)-2-pyridinyloxy]phenoxy]propionate;
ethyl 2-[4-[(6-chloro-2-benzoxazolyl)oxy]phenoxy]propanoate;
butyl 2-[4-[[5-(trifluoromethyl)-2-pyridinyl]oxy]phenoxy]propionate;
2-[4-[(6-chloro-2-quinoxalinyl)oxy]phenoxy]propionic acid, ethyl ester;

URACILS 5-bromo-3-s-butyl-6-methyluracil;
5-bromo-3-cyclohexyl-1,6-dimethyluracil;
3-cyclohexyl-5,6-trimethyleneuracil;
5-bromo-3-isopropyl-6-methyluracil;
3-tert-butyl-5-chloro-6-methyluracil;

NITRILES 2,6-dichlorobenzonitrile;
diphenylacetonitrile;
3,5-dibromo-4-hydroxybenzonitrile;
3,5-diiodo-4-hydroxybenzonitrile;

OTHER ORGANIC HERBICIDES 2-chloro-N,N-diallylacetamide;
N-(1,1-dimethyl-2-propynyl)-3,5-dichlorobenzamide;

maleic hydrazide;
3-amino-1,2,4-triazole;
monosodium methanearsonate;
disodium methanearsonate;
N,N-dimethyl-α,α-diphenylacetamide;
N-N-di(n-propyl)-2,6-dinitro-4-(trifluoromethyl)aniline;
N,N-di(n-propyl)-2,6-dinitro-4-methylaniline;
N,N-di(n-propyl)-2,6-dinitro-4-methylsulfonylaniline;
O-(2,4-dichlorophenyl)-O-methyl isopropylphosphoramidothioate;
4-amino-3,5,6-trichloropicolinic acid;
2,3-dichloro-1,4-naphthoquinone;
di(methoxythiocarbonyl)disulfide;
3-(1-methylethyl)-1H-2,1,3-benzothiadiazin-(4)3H-one-2,2-dioxide;
6,7-dihydrodipyridol[1,2-a:2',1'-c]pyrazidiium salts;
1,1'-dimethyl-4,4'-bipyridinium salts;
3,4,5,6-tetrahydro-3,5-dimethyl-2-thio-2H-1,3,5-thiadiazine;
2-[1-(ethoxyimino)butyl]-5-[s-(ethylthio)propyl]-3-hydroxy-2-cyclohexen-1-one;
2-(2-chlorophenyl)methyl-4,4-dimethyl-3-isoxazolidinone;
N-(1-ethylpropyl)-3,4-dimethyl-2,6-dinitrobenzamide;
4-chloro-5-(methylamino)-2-(α,α,α-trifluoro-m-toluyl)-3-(2H)-pyridazinone; and
2-(3,5-dichlorophenyl)-2-(2,2,2-trichloromethyl)oxirane.

When mixtures of herbicides are employed, the relative proportions which are used will depend upon the crop to be treated and the degree of selectivity in weed control desired.

It is to be understood that changes and variations in this invention may be made without departing from the spirit and scope of this invention as defined by the appended claims.

We claim:

1. A compound of the formula

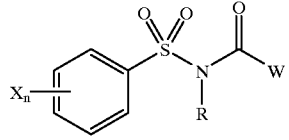

(I)

wherein

W is a heterocyclyl moiety selected from pyridyl substituted with a halo($C_1$–$C_6$)alkyl vicinal to the carbonyl group, and all optionally further substituted with from 1 to 3 substituents selected from Z, R is ($C_3$–$C_6$)alkynyl or epoxy($C_3$–$C_6$)alkyl, n is 0, 1, 2, or 3, and X and Z are each independently halo, ($C_1$–$C_6$)alkyl, halo($C_1$–$C_6$)alkyl, ($C_1$–$C_6$)alkoxy, halo($C_1$–$C_6$)alkoxy, nitro, cyano or ($C_1$–$C_6$)alkoxycarbonyl.

2. The compound of claim 1 wherein W is pyridyl substituted with trifluoromethyl vicinal to the carbonyl group, R is propargyl or 2,3-epoxypropyl, n is 1, and X and Z are each independently halo or methyl.

3. The compound of claim 2 wherein W is 4-(trifluoromethyl)-3-pyridyl, R is propargyl, and X is 3-chloro or 3-methyl.

4. The compound of claim 3 which is 3-chloro-N-propargyl-N-(4-(trifluoromethyl)pyridine-3-carbonyl)benzenesulfonamide.

5. The compound of claim 3 which is 3-methyl-N-propargyl-N-(4-(trifluoromethyl)pyridine-3-carbonyl)benzenesulfonamide.

6. A herbicidal composition comprising a herbicidally effective amount of a compound of claim 1 and an agronomically acceptable carrier.

7. The composition of claim 6 further comprising a fertilizer or fertilizing material.

8. A method of controlling a weed comprising applying a herbicidally effective amount of a composition of claim 6 to the weed, to the locus of the weed or to the growth medium of said weed.

9. The method of claim 8 wherein the locus of the weed is in a corn, cotton, rice, soybean or wheat crop.

* * * * *